United States Patent [19]
Cohen

[11] Patent Number: 5,860,937
[45] Date of Patent: Jan. 19, 1999

[54] EVACUATED SAMPLE COLLECTION TUBE WITH AQUEOUS ADDITIVE

[75] Inventor: Richmond R. Cohen, Wanaque, N.J.

[73] Assignee: Becton, Dickinson & Company, Franklin Lakes, N.J.

[21] Appl. No.: 846,343

[22] Filed: Apr. 30, 1997

[51] Int. Cl.$^6$ .............................. A61B 5/00; B01D 21/26
[52] U.S. Cl. .......................... 600/576; 600/583; 210/782; 210/359; 210/516; 422/101
[58] Field of Search ..................... 604/317, 411, 604/415; 600/573, 576, 577, 578, 583; 210/359, 398, 516, 782; 422/101, 73, 57

[56] References Cited

U.S. PATENT DOCUMENTS

| | | | |
|---|---|---|---|
| 2,460,641 | 2/1949 | Kleiner | 128/214 |
| 2,618,264 | 11/1952 | Bloxsom . | |
| 3,661,265 | 5/1972 | Greenspan | 210/359 |
| 3,814,248 | 6/1974 | Lawhead | 210/83 |
| 3,897,337 | 7/1975 | Ayres | 210/136 |
| 3,972,812 | 8/1976 | Gresl, Jr. | 210/77 |
| 4,443,345 | 4/1984 | Wells | 210/782 |
| 4,492,634 | 1/1985 | Villa-Real | 210/398 |
| 4,522,713 | 6/1985 | Nussbaumer et al. | 210/136 |
| 5,634,474 | 6/1997 | Grippi | 600/573 |

Primary Examiner—John G. Weiss
Assistant Examiner—David J. Cho
Attorney, Agent, or Firm—Arthur D. Dawson

[57] ABSTRACT

An assembly for collection of a sample of a body fluid from a subject's body of the present invention includes a hollow tube defining an axis with an open end and a closed end. The hollow tube defines a chamber therewithin for receiving a sample of a collected fluid from a subject. The tube has a resilient closure disposed in the open end to close the chamber and to form a seal capable of maintaining a pressure differential between atmospheric pressure and a pressure less than atmospheric pressure within the chamber. The chamber contains an aliquot of an aqueous additive for treating the fluid sample. The chamber also includes a matrix formed from a fibrous material having capillary spaces therein for absorbing the aliquot of the aqueous additive and an aliquot of a water immiscible liquid with a density greater than about 1.07 grams per milliliter to encapsulate the aqueous additive absorbed on the matrix. The tube has a normally closed resilient valve disposed in the chamber to contain the aqueous additive, the liquid and the matrix between the closed tube end and the valve. The valve is openable by centrifugation when there is a sample in the tube thereby allowing the lower density fractions of the sample and the aqueous additive to collect above the valve and to mix.

18 Claims, 7 Drawing Sheets

EVACUATED SAMPLE COLLECTION TUBE WITH AQUEOUS ADDITIVE

FIELD OF INVENTION

This invention generally relates to collection of body fluid samples for analysis. More particularly, the invention relates to evacuated fluid sample collection tubes having aqueous additives therein for preparing the collected sample for analysis.

BACKGROUND

Evacuated sample collection tubes have been in general usage in the United States for almost fifty years. Initially, as disclosed in U.S. Pat. No. 2,460,641 to Klienert, the sample collection tube was simply an evacuated glass test tube with a resilient stopper and intended for use in blood collection. As practitioners recognized the utility of these evacuated blood collection tubes, (trade named "VACUTAINER" and available from Becton, Dickinson and Company, Franklin Lakes, N.J.) the tubes are now supplied with various additives already in them to prepare the blood specimen for a particular test. The tubes now are also evacuated to selected less than atmospheric pressures to provide a preselected volume of blood drawn. The most widely used tubes are evacuated to provide a blood withdrawal volume of about four and one half milliliters.

One commonly used additive tube is termed a "coagulation" tube. According to a widely followed convention, these coagulation tubes contain a sufficient amount of buffered citrate in aqueous saline to provide a ratio of about 9:1 of blood to aqueous citrate. Coagulation tubes are often used to collect blood samples to assess the need for or to adjust the dosage of anticoagulant medications. When the freshly drawn blood contacts the citrate, the cellular fraction, i.e., red blood cells, platelets and white blood cells precipitate, leaving plasma as the supernatant liquid after the tube is centrifuged. Commonly, an aliquot of this plasma is then subjected to treatment with a coagulation agent such as thromboplastin reagent or similar and the time to clot is measured. These time to clot determinations are called the prothrombin time ("P.T.") and activated partial thromboplastin time ("A.P.T.T.").

More recently, clinical testing practitioners have recognized the hazards associated with blood-borne pathogens and manufacturers have begun to supply blood collection tubes from materials less likely to be broken by inadvertent mishandling than the original glass tubes. Evacuated blood collection tubes are now supplied formed from thermoplastic resins such as polyethylene terephthalate (PET) and similar materials. While these thermoplastic resin tubes have reduced the chance of breakage by inadvertent mishandling, the use of thermoplastic resin tubes to replace glass causes other problems. Some thermoplastic materials were found not to be capable of withstanding the stress of vacuum, other materials are permeable in varying degrees to gases such as oxygen, water vapor and the like. When the tube material is permeable to gases, the transmission into the tube of oxygen or nitrogen results in gradual loss of the vacuum. In the case of the citrate coagulation tubes and other tubes with aqueous additives, loss of water vapor through the tube wall during shelf storage results in changing the concentration of the aqueous additive. In the case of the coagulation tube, once the concentration of the aqueous saline buffer changes appreciably, the ratio of blood drawn to the aqueous saline buffer no long follows the convention of the 9:1 ratio, rendering the tube unsatisfactory for use. The loss of water through the tube wall has proved to be the limiting factor for thermoplastic coagulation tube shelf life.

The water loss problem through thermoplastic coagulation tubes has been addressed by two current commercial suppliers. One supplier, Terumo, Elkton, Md. supplies their thermoplastic coagulation tubes in a sealed tub containing about 15 tubes. As long as the tub is sealed, the water loss through the tubes is controlled, providing a usable shelf life. Once the tub is unsealed, the tubes begin to lose water through the tube walls. As a result, practitioners need to use up these tubes within a few weeks once the tub is opened. Another supplier, Greiner GMBH, Frickenhausen, Germany, provides a thermoplastic coagulation tube formed from two separate independently formed layers, one inside the other. In the Greiner tube, the inner tube is formed from polypropylene, a material that is substantially non-permeable to water vapor, and the outer layer is PET. The two layer tube provides a satisfactory shelf life by limiting water vapor transmission, but the manufacture and assembly of the two components into the two-layer tube is inefficient compared to a single layer tube.

If a single layer thermoplastic tube was available that limited water loss from tube additives, thus providing a shelf-life similar to that of borosilicate glass tubes with similar additives, the art of blood collection tubes would be advanced. Such a tube is disclosed herein below.

SUMMARY

An evacuated device for collection of a sample of a body fluid from a subject's body of the present invention includes a hollow tube defining an axis with an open end and a closed end. The hollow tube defines a chamber therewithin for receiving a sample of a collected fluid from a subject. There is a resilient closure disposed in the open end of the tube to close the chamber and to form a seal capable of maintaining a pressure differential between atmospheric pressure and a pressure less than atmospheric pressure within the chamber. The chamber contains an aliquot of an aqueous additive for treating the fluid sample. The chamber also includes a matrix formed from a fibrous material having capillary spaces therein for absorbing the aliquot of the aqueous additive and an aliquot of a water immiscible liquid with a specific gravity greater than about 1.07 to encapsulate the aqueous additive absorbed on the matrix. The tube has a normally closed resilient valve disposed in the chamber to contain the aqueous additive, the liquid and the matrix between the closed tube end and the valve. The valve is openable by centrifugation when there is a sample in the tube thereby allowing the lower density fractions of the sample and the aqueous additive to collect above the valve and to mix.

The device of the invention provides the ability to manufacture an aqueous additive containing blood collection tube with comparable shelf stability to glass tubes with aqueous additives. The device of the invention substantially reduces the risk of breakage caused by inadvertent mishandling of glass tubes while giving practitioners functional performance similar to the current widely used aqueous additive tubes. As a result of this disclosure, practitioners of clinical testing are now aware that the disclosed tube functions similarly for many other aqueous additive systems suitable for blood or other body fluid samples. The use of aqueous coagulation reagents is intended to be illustrative and not limitative of the invention.

DETAILED DESCRIPTION

While this invention is satisfied by embodiments in many different forms, there is shown in the drawings and herein described in detail a preferred embodiment of the invention with the understanding that the present disclosure is to be considered exemplary of the principles of the invention and is not intended to limit the invention to the embodiment illustrated. The scope of the invention is measured by the appended claims and their equivalents.

Referring to FIGS. 1–6, an assembly 10 for collection of a sample 20 of a body fluid from a subject's body of the present invention includes a hollow tube 12 defining an axis A having an open end 14 and a closed end 16 defining a chamber 18 therein for receiving sample 20 of a collected fluid from a subject. Tube 12 has a resilient closure 24 disposed in open end 14 to close chamber 18 and to form a seal 26 capable of maintaining a pressure differential between atmospheric pressure and a pressure less than atmospheric pressure within chamber 18. Preferably, closure 24 includes a shield 25 to substantially reduce any tendency of a sample contained in chamber 18 to spatter when resilient closure 24 is removed for access to the sample. Assembly 10 includes an aliquot of an aqueous additive 28 for treating the fluid sample. Suitable additives include, but are not limited to, organic acids, salts of organic acids, alkali metal salts of halides, organic chelating agents, fluorescent dyes, antibodies, binding agents or any other reagent or combination of reagents normally used to treat body fluid samples for analysis. Assembly 10 also includes a matrix 30 preferably formed from a fibrous material 32 having capillary spaces 33 therein for absorbing aqueous additive 28. Tube 10 also has an aliquot of a substantially water immiscible liquid 34 that has a specific gravity greater than about 1.07 for encapsulating aqueous additive 28 absorbed in matrix 30. Assembly 10 also includes a normally closed resilient valve 36 disposed in chamber 18 to contain the aqueous additive, the liquid and the matrix between closed end 16 and valve 36. Valve 36 is openable by centrifugation of tube 10, schematically illustrated by the "G" in FIG. 4, when the sample is in chamber 18 thereby allowing lower density fractions of the sample and the aqueous additive to collect above valve 36 and to mix. Preferably, valve 36 includes an area of reduced thickness 38 with at least one slit 40 that is openable under centrifugation conditions. The applied centrifugation is preferably greater than about 2500 R.C.F. (2500 times the acceleration due to gravity). In the example where the aqueous additive is buffered citrate in aqueous saline and the sample is freshly drawn blood, a lower density fraction 42 includes plasma and the aqueous citrate. Assembly 10 of the invention is suitable for other body fluid samples and other aqueous additives.

An example using the assembly of the invention for obtaining plasma samples suitable for coagulation studies is given below. In this example, the preferred perfluoropolyether serves to encapsulate the aqueous reagent, substantially reducing transmission of water vapor through tube 12 that is formed from polyethyleneterephthalate. The preferred use of the particular materials for a coagulation tube is intended to be illustrative of an application of the invention and not limitative of the invention to just coagulation sample assemblies or to tubes formed from PET.

Materials List

1. Suitable high density water immiscible (hydrophobic) liquids 34 with a relatively low vapor pressure at ambient temperatures having a specific gravity at 20° C. greater than about 1.07 include but are not limited to benzyl benzoate, perfluoropolyethers, poly(methyl-3,3,3-trifluoropropylsiloxane), dipropyl benzoate, dimethyl benzoate, dimethyl malonate, phenyl acetate, anisaldehyde and the like. The specific gravity value of greater than about 1.07 is selected because the cellular blood components have a specific gravity between about 1.05 to 1.07. The preferred material is a low vapor pressure non-hemolytic perfluoropolyether, formula weight between about 2,000–15,000 Atomic Mass Units, density at 20° C. between about 1.85–1.90 gms./ml. Suitable perfluoropolyethers are available from Ausimont USA, Morristown, N.J. (FOMBLIN); PCR, Inc., Gainesville, Fla. (AFLUNOX); and E.I.Dupont, Wilmington, Del. (KRYTOX).

2. Suitable matrix materials 30 have large surface area relative to their mass, are substantially hydrophilic and include, but are not limited to: fibrous materials such as cotton, polyester staple fibers, glass fiber staple, glass fiber cloth, polyamide staple fibers and cellulosic staple fibers and the like; inert hydrophilic foams such as polyurethanes, polyvinyl alcohol and the like; and cellulosic papers such as filter papers and the like. The preferred material for matrix 30 is glass fiber staple strand 1000–2500 yards per pound such as is available from Owens Corning (VITRON) with a filament diameter between about 0.00021–0.00028 in., a bulk density between about 300 to about 500 grams per kilometer and a nominal yardage of about 1500 yards per pound. The glass fiber staple strand is preferred for this application because it has a large surface area relative to its mass, allowing the aqueous saline solution to spread on the surface of the matrix.

3. Physiological saline solution for aqueous additive 28, 0.9 percent aqueous sodium chloride with a pH between about 7.0–7.2.

4. Resilient Elastomers suitable for the valve include but are not limited to Santoprene 8211-35, 8201-60 or equivalent, Monsanto, St. Louis, Mo. and Silastic silicone elastomer, Dow-Corning, Midland, Mich. or equivalent. Shore A durometer between about 50 and 100.

5. Citric acid monohydrate, ACS reagent grade or equivalent.

6. Sodium Oxalate dihydrate, ACS reagent grade or equivalent.

7. Sodium Citrate, ACS reagent grade or equivalent.

8. Potassium Sorbate, ACS reagent grade or equivalent.

9. Disodium ethylenediaminetetraacetic acid (EDTA), ACS reagent grade or equivalent.

10. Sodium fluoride, ACS reagent grade or equivalent.

11. Potassium chloride, ACS reagent grade or equivalent.

12. Materials suitable for forming closed end cylindrical tube 12 of a suitable thickness and size include, but are not limited to, substantially transparent thermoplastic materials such as polycarbonate, polypropylene, polyethyleneterephththalate and the like. For the purpose of these examples tube 12 being formed from Polyethyleneterephthalate tube (PET) with a 13 mm diameter with a 100 mm length is preferred, other sizes and other materials may be preferred for other applications.

13. Resilient elastomeric closure 24 is sized to fit the tube and maintain an interior pressure below atmospheric pressure. Suitable materials include, but are not limited to, silicone rubber, natural rubber, styrene butadiene rubber (SBR), ethylene-propylene dimer monomer (EPDM), polychloroprene and the like. Natural rubber is preferred for closure 24 for the illustrated application.

14. Polypropylene, polyvinylchloride, polyethylene and the like are suitable thermoplastic materials for forming stopper shield 25. Polyethylene is preferred for shield 25 in this application. Stopper shield 25 preferably has an outer skirt sized to extend beyond and cover a portion of the outside surface of the tube adjacent to the open end as the closure is removed from the tube. By extending over and covering the portion of the tube, shield 25 serves to reduce the potential for sample spatter when elastomeric closure 24 is removed from the open end of the tube.

15. Purified water, USP or equivalent.

EXAMPLE

A. Materials: PET tube 13 mm×100 mm; natural rubber resilient stopper; polyethylene stopper shield; glass fiber staple strands; perfluoropolyether (Fomblin M60); 1.29M aqueous buffered sodium citrate, physiological saline solution, potassium sorbate.

B. Assembly: With tube held vertically, deliver about 0.25 ml aliquot of perfluoropolyether liquid 34 into bottom of tube 12. Position about 0.5 grams glass fiber matrix 30 in tube above liquid 34. Slowly deliver 0.5 ml aqueous saline 28 onto glass fiber matrix 30 to allow the solution to wet matrix 30. Deliver about 0.75 ml of perfluorpolyether liquid 34 over aqueous saline 28 and glass fiber matrix 30. Position elastomeric valve 36 in tube 12 to substantially contain glass fiber matrix 30, aqueous saline 28 and perfluoropolyether liquid 34 against closed tube end 16. Preferably, valve 36 is positioned with area of reduced thickness 38 positioned toward open end 14 of tube 12. Preferably, valve 36 has a larger outside diameter "Y" than an inside diameter "X" of chamber 18 within tube 12. Thus, when valve 36 is positioned within the tube, the difference in diameters results in an interference fit between the tube and the valve to retain valve 36 as positioned. This position for valve 36 substantially eliminates entrapment of air between the perfluoropolyether liquid 34 and valve 36. Introduce about 0.05 ml of 1.29M aqueous citrate buffer into tube above the valve. In this embodiment, the water substantially evaporates from the citrate buffer leaving a substantially dry residue 29 above valve 36 that mixes with the sample when it is introduced into chamber 18. Evacuate chamber 18 to a pressure below atmospheric pressure sufficient to provide a 4.5 ml blood draw and insert resilient closure 24 with stopper shield 25 to retain the pressure differential.

C. Usage: Introduce a blood sample into the assembly 10 of the invention following conventional phlebotomy practice using a phlebotomy needle 50. Place assembly 10 in a suitable centrifuge and apply between about 2000 to about 3000 R.C.F. to the tube containing the sample as is generally done with conventional tubes. Under centrifugation, the higher density materials migrate to the bottom of the tube and the lower density materials migrate upwardly. The effect of these migrations on the tube containing the blood sample is that cellular components 60 of the blood sample move toward the tube bottom through the resilient valve and the aqueous saline moves upwardly and mixes with the blood plasma and the citrate. Additionally, the high density perfluoropolyether liquid 34 remains at tube closed end 16 along with the matrix. At the completion of the centrifugation, the valve returns to the normally closed position and the blood plasma component, in the conventional ratio of about 9:1 blood to aqueous citrate is topmost and, as the lowest density fraction, may be removed to conduct conventional coagulation studies.

In selection of the high density low vapor pressure liquid for use as an encapsulant, consideration should be made as to the compatibility of the liquid with the material selected for the tube and for the absorptive matrix. Chemical or physical interactions between one or another of these components may adversely effect the performance of the invention. Additionally, the compatibility of the high density low vapor pressure liquid with the particular sample and tests to be run on the sample must be evaluated. If the high density low vapor pressure liquid is entrained by the sample, it may adversely effect the results of subsequent testing on the sample. Similar considerations should be made regarding interactions between the matrix materials and the liquid, the sample and the matrix, the material selected for the valve, the reagents and all components as well as any effects of radiation, or other sterilization conditions.

Figure 1:
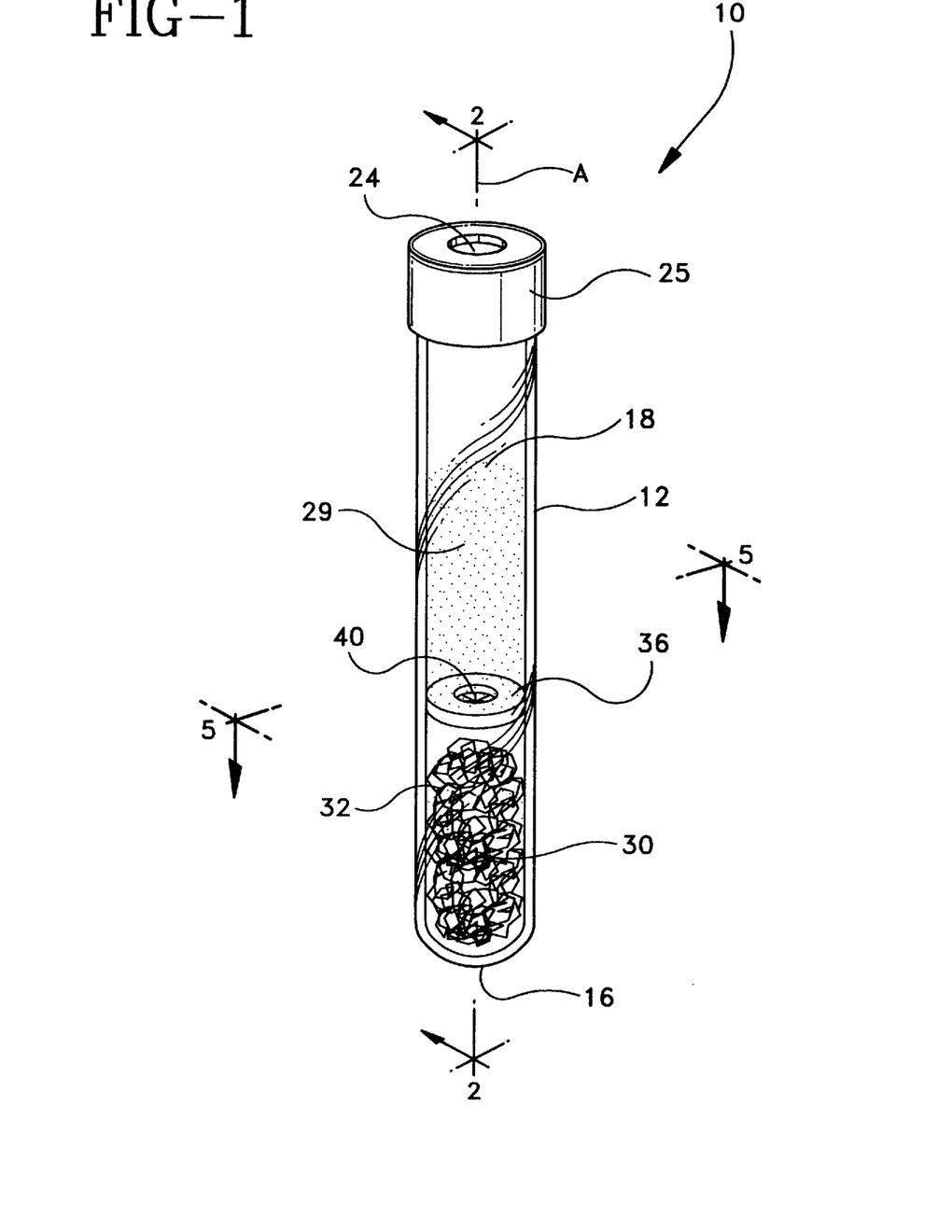
FIG. 1 is a perspective view of the evacuated sample collection assembly of the invention.
Figure 1A:
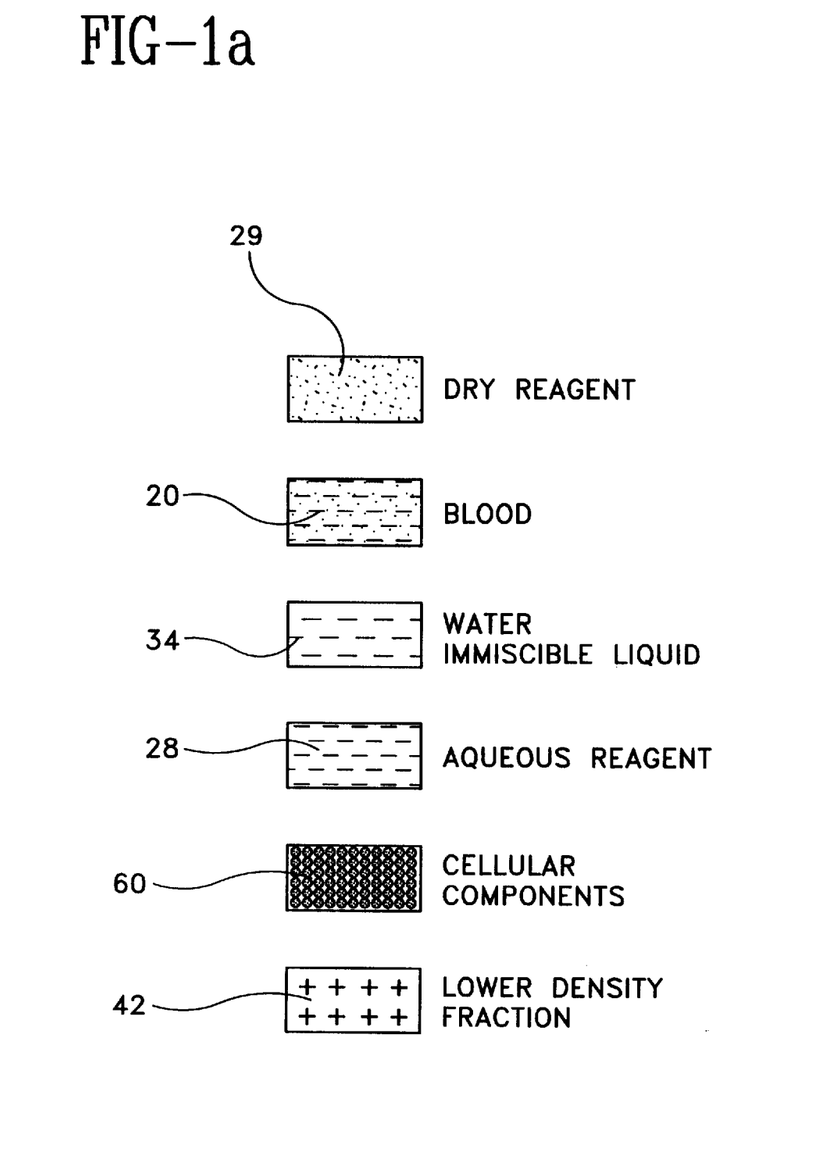
FIG. 1a is a key to various graphical elements used in FIGS. 1–4
Figure 2:
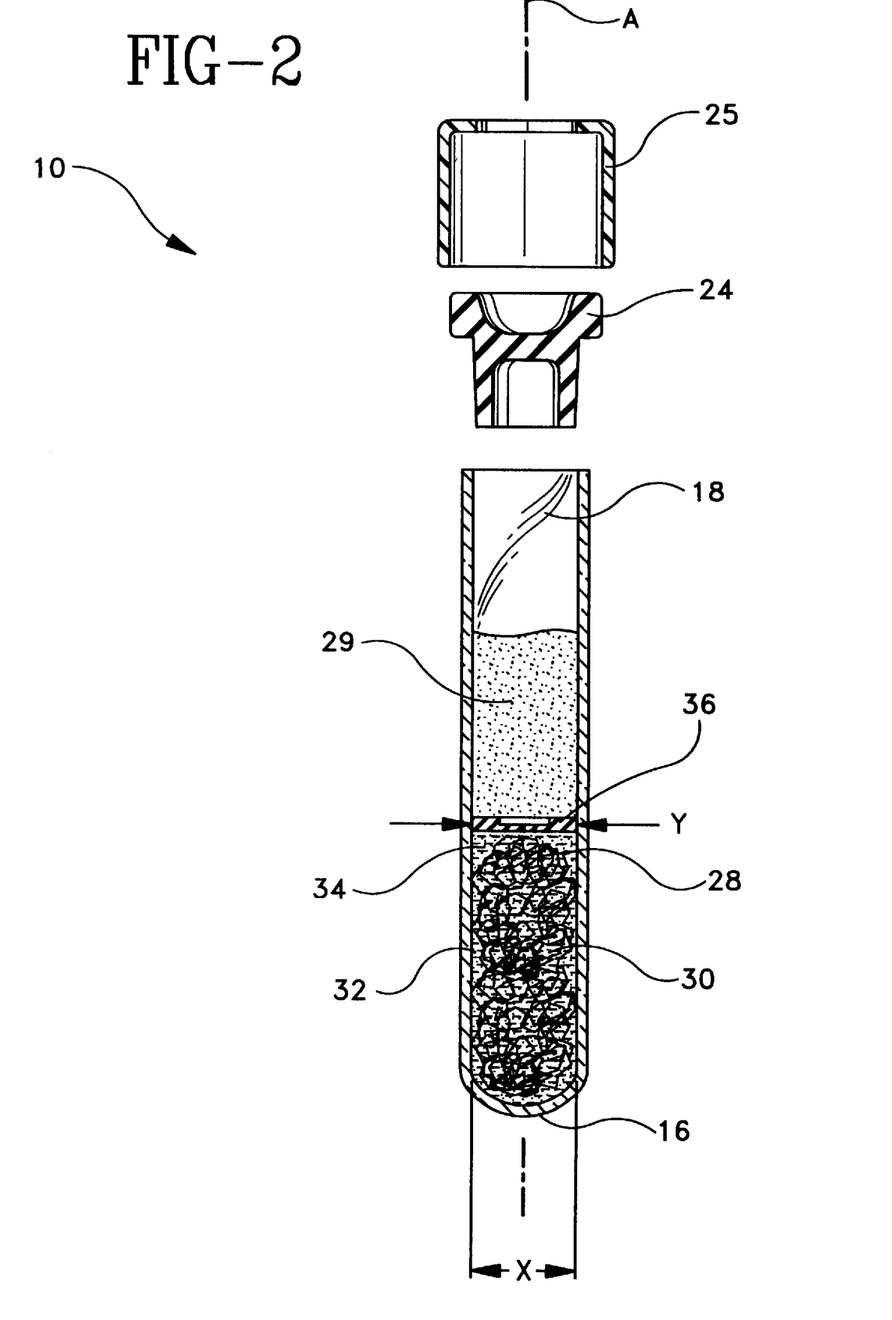
FIG. 2 is an exploded cross-sectional view of the invention of FIG. 1 taken along the line 2—2.
Figure 2A:
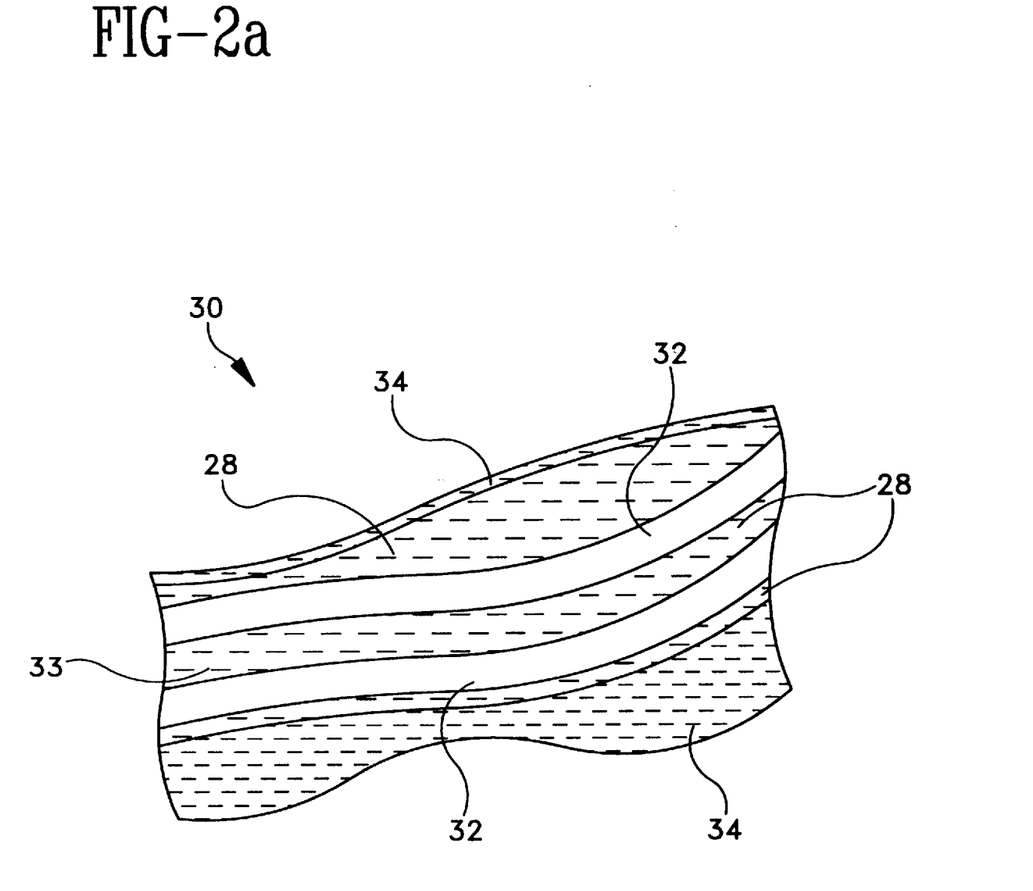
FIG. 2a is an enlarged schematic view of a portion of the matrix component of the invention from FIGS. 1 and 2.
Figure 3:
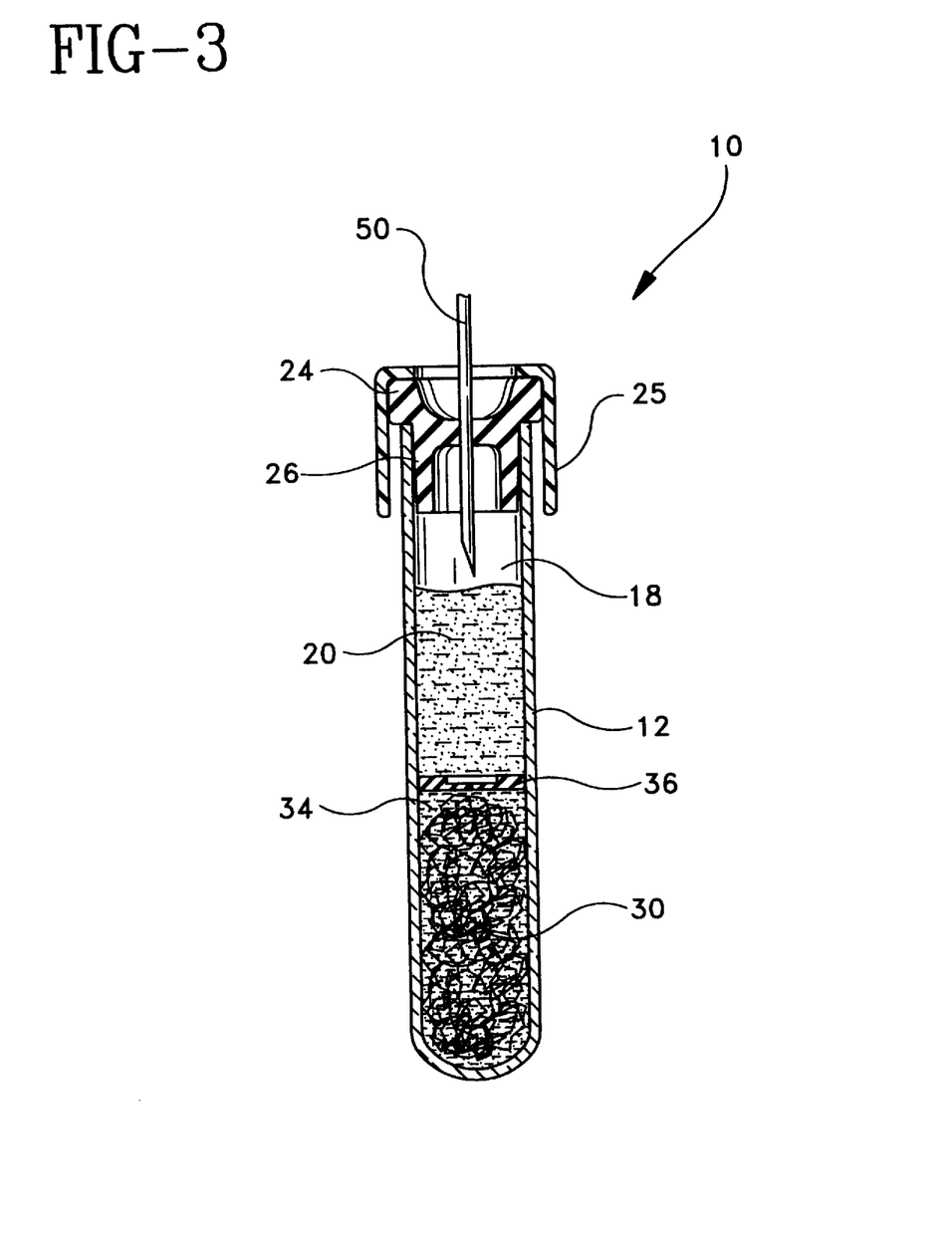
FIG. 3 is a cross-sectional view of the evacuated assembly of FIG. 1 being charged with a fluid sample.
Figure 4:
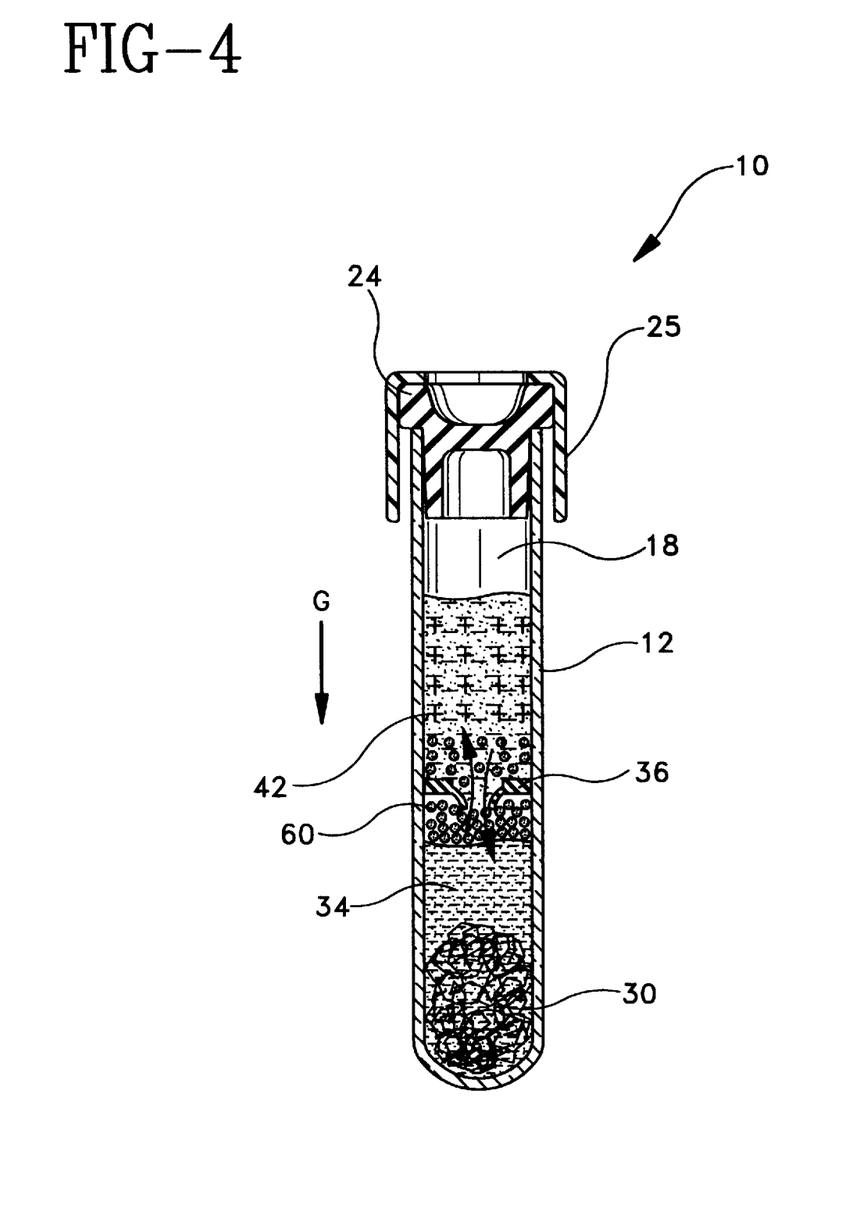
FIG. 4 is a cross-sectional view of the assembly of FIG. 1 charged with a sample while under centrifugation.
Figure 5:
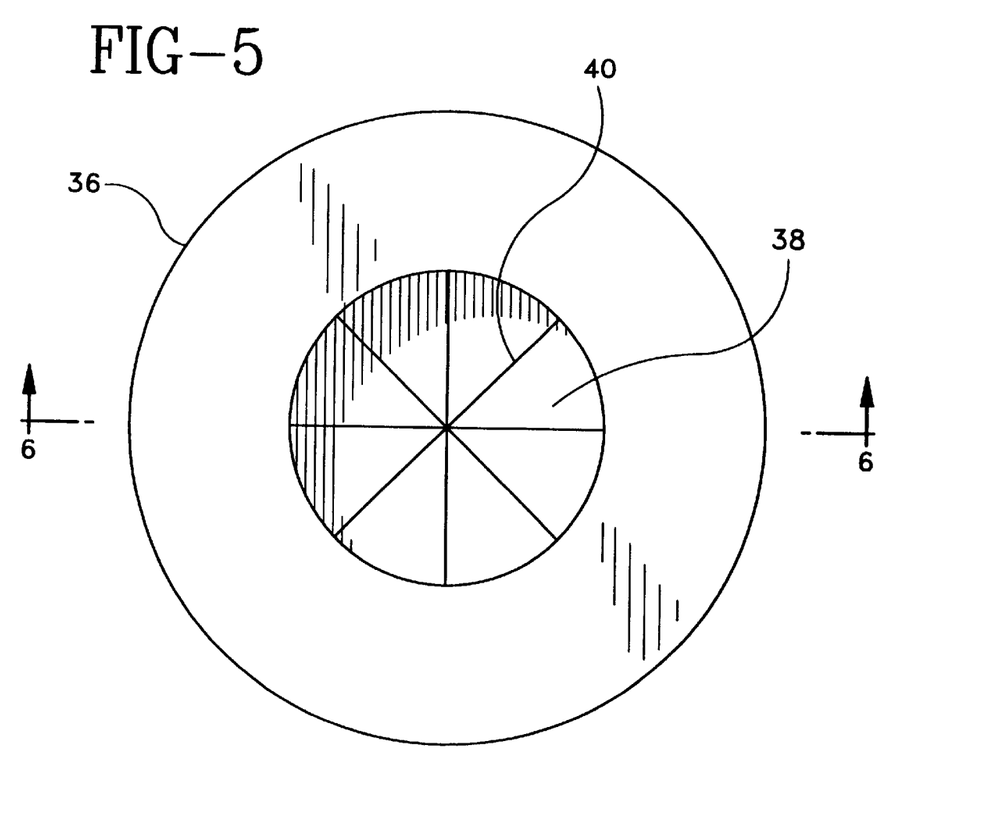
FIG. 5 is a top plan view of the assembly of FIG. 1 taken along the line 5—5.
Figure 6:
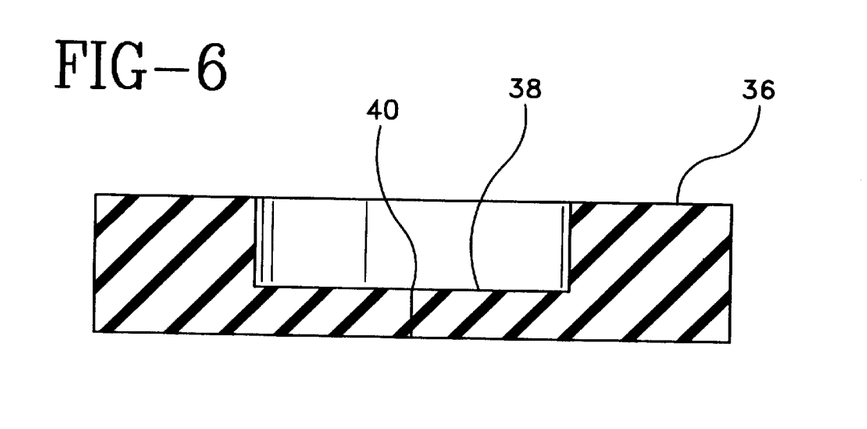
FIG. 6 is a cross-sectional view of the assembly from FIG. 5 taken along the line 6—6.

Materials selection studies: Compatibility was determined between the high density low vapor pressure liquid 34 with tube materials; with blood samples; and the matrix material. In the compatibility testing conducted for selection of the preferred embodiment for liquid 34, perfluoropolyether was found not to have unfavorable interactions with PET, or cause hemolysis of blood. In testing of diethyl benzoate, dimethyl malonate, phenyl acetate, anisaldehyde and diethyl malonate for compatibility with PET, all showed some degree of interaction, as exhibited by the PET tube turning cloudy or white. Additionally, as illustrated in FIG. 2a, the perfluorpolyether was found to be effective in encapsulation of the aqueous saline and substantially reduce the loss of water through the PET tube 12. For this application, e.g., benzyl benzoate for liquid 34 was not satisfactory because slight hemolysis of blood samples was observed. Examination of cotton fibers and filter paper for matrix 30 showed that there was insufficient absorbence of the aqueous saline and the release of the absorbed saline was unsatisfactory under centrifugation.

The fluid collection assembly of the invention performs similarly to conventional fluid collection assemblies with tubes formed from borosilicate glass. Assembly 10 of the invention by use of encapsulant liquid 34, matrix 30 and valve 36 provides practitioners of blood collection and analysis with the ability to use thermoplastic tubes that are less prone to be broken by inadvertent mishandling while maintaining the expected performance delivered by conventional glass evacuated blood collection assemblies.

What is claimed is:

1. An evacuated assembly for collection of a sample of a body fluid from a subject's body comprising:

a hollow tube defining an axis having an open end and a closed end defining a chamber therein for receiving a sample of a collected fluid from a subject;

a resilient closure disposed in said open end to close said chamber and to form a seal capable of maintaining a pressure differential between atmospheric pressure and a pressure less than atmospheric pressure within said chamber;

an aliquot of an aqueous additive for treating the fluid sample;

a matrix formed from a fibrous material having capillary spaces therein for absorbing said aliquot of said aqueous additive;

an aliquot of a water immiscible liquid having a specific gravity greater than about 1.07 for encapsulating said aqueous additive absorbed on said matrix; and a normally closed resilient valve disposed in said chamber to contain said aqueous additive, said liquid and said matrix between said closed end and said valve, said valve being openable when the sample is in said chamber by centrifugation of said tube thereby to allow lower density fractions of the sample and said aqueous additive to collect above said valve and to mix.

2. The assembly of claim 1 wherein said liquid is selected from the group consisting of organic esters, silicone oils and perfluoropolyether fluids having a formula weight between about 2,000 and about 13,000 atomic mass units.

3. The assembly of claim 2 wherein said liquid is a perfluoropolyether with a density between about 1.6 to about 1.9 grams per cubic centimeter.

4. The assembly of claim 1 wherein said hollow tube is formed from a thermoplastic resin.

5. The assembly of claim 1 wherein said matrix is selected from the group consisting of glass staple strand, glass wool, cotton fibers, nylon fibers and combinations thereof.

6. The assembly of claim 5 wherein said matrix is glass staple strand having about a ten micron average diameter, a bulk density of between about 330 grams per kilometer and a nominal yardage of about 1500 yards per pound.

7. The assembly of claim 1 wherein said normally closed resilient valve is formed from an elastomeric material selected from the group consisting of natural rubber, thermoset synthetic elastomers and thermoplastic elastomers.

8. The assembly of claim 7 wherein said normally closed resilient valve is formed from a thermoplastic elastomer having the shape of a disc with an outer section and a center section, said center section having a thickness less than the thickness of said outer section.

9. The assembly of claim 8 wherein said normally closed valve further comprises at least one diametric slit in said center section, so that when said tube contains the sample and is subjected to centrifugation of said tube at about 2,000 to about 3,000 RCF, said valve allows said aliquot of said aqueous additive to mix with the sample.

10. The assembly of claim 9 where in said hollow tube has an inside diameter and said valve has an outside diameter larger than said inside diameter of said tube thereby providing an interference fit to retain said valve substantially normal to said axis in said chamber.

11. The assembly tube of claim 1 wherein said aqueous additive further comprises materials selected from the group consisting of citric acid, oxalic acid, salts of citric acid and oxalic acid, sodium chloride, potassium chloride, disodium ethylenediaminetetraacetic acid, sodium fluoride and combinations thereof.

12. The assembly of claim 1 further comprising a portion of a sample modifying reagent disposed in said chamber between said resilient valve and said open top of said tube so that when the sample is introduced into said chamber, the modifying reagent contacts the sample.

13. The assembly of claim 1 wherein said hollow tube includes an outside surface and said resilient closure further includes a formed thermoplastic shield having, an axial opening therethrough to provide access to said resilient closure and an outer skirt sized to cover a portion of said outside surface adjacent said open end of said tube so that when said resilient closure is removed from said open end, said skirt extends beyond said closure.

14. An evacuated blood collection assembly comprising:

a hollow tube defining an axis having an open end and a closed end defining a chamber therein for receiving a blood sample from a subject;

a resilient closure disposed in said open end to close said chamber and to form a seal capable of maintaining a pressure differential between atmospheric pressure and a pressure less than atmospheric pressure within said chamber;

an aliquot of an aqueous additive for treating the fluid sample;

a matrix formed from a fibrous material having capillary spaces therein for absorbing said aliquot of said aqueous buffered citrate;

an aliquot of a substantially water immiscible perfluoropolyether having a density between about 1.6 to about 1.9 grams per milliliter for encapsulating said aqueous additive absorbed on said matrix; and a normally closed resilient valve disposed in said chamber to contain said aqueous buffered citrate, said perfluoropolyether and said matrix between said closed bottom and said valve, said valve being openable toward said closed bottom of said tube when the sample is in said chamber by centrifugation of said tube at about 2,000 to about 3,000 RCF thereby to allow lower density fractions of the sample and said aqueous buffered citrate to collect above said valve and to mix.

15. The assembly of claim 14 wherein said aqueous additive comprises saline solution and buffered citrate.

16. The assembly of claim 14 wherein said pressure differential between atmospheric pressure and said pressure in said chamber is preselected to provide a blood draw sample sufficient to provide a ratio of blood to said aliquot of aqueous additive of about nine to about one.

17. The assembly of claim 15 wherein said hollow tube is formed from a thermoplastic resin.

18. The assembly of claim 17 wherein said thermoplastic resin is polyethyleneterephthalate.

* * * * *